(12) United States Patent
Burkamp et al.

(10) Patent No.: US 6,852,718 B2
(45) Date of Patent: Feb. 8, 2005

(54) PHENYLSULPHONYLIPIPERAZINYL DERIVATIVES AS 5-HT RECEPTOR LIGANDS

(75) Inventors: Frank Burkamp, Bishops Stortford (GB); Susan Koon-Fung Cheng, Bietighim-Bissingen (DE); Stephen Robert Fletcher, Bishops Stortford (GB)

(73) Assignee: Merck Sharp & Dohme Ltd, Hoddesdon ( * ) Notice: Subject to any disclaimer, the term of this patent is extended or adjusted under 35 U.S.C. 154(b) by 0 days.

(21) Appl. No.: 10/333,285

(22) PCT Filed: Mar. 30, 2001

(86) PCT No.: PCT/GB01/01472

§ 371 (c)(1),
(2), (4) Date: Apr. 21, 2003

(87) PCT Pub. No.: WO01/74797

PCT Pub. Date: Oct. 11, 2001

(65) Prior Publication Data

US 2003/0181464 A1 Sep. 25, 2003

(30) Foreign Application Priority Data

Mar. 31, 2000 (GB) ............................................. 0007907

(51) Int. Cl.$^7$ ..................... A61K 31/495; C07D 295/26
(52) U.S. Cl. .................... 514/235.8; 544/383; 544/121; 544/360; 544/372; 544/238; 544/295; 544/357; 544/366; 544/367; 544/369; 544/370; 544/371; 514/252.12; 514/253.01; 514/254.01
(58) Field of Search ................................. 544/383, 121, 544/360, 372; 514/252.12, 235.8, 253.01, 254.01

(56) References Cited

U.S. PATENT DOCUMENTS

| 4,218,455 A | 8/1980 | Wise et al. |
| 4,616,086 A | 10/1986 | Witte et al. |
| 5,134,149 A | 7/1992 | Carr et al. |
| 5,641,779 A | 6/1997 | Halazy et al. |
| 5,849,912 A | 12/1998 | Akasaka et al. |
| 2003/0130287 A1 * | 7/2003 | Ackermann et al. ... 514/253.07 |

FOREIGN PATENT DOCUMENTS

| WO | WO 91/18602 | 12/1991 |
| WO | WO 00/43362 | 7/2000 |
| WO | 2001/051469 | * 7/2001 |

OTHER PUBLICATIONS

Ackermann et al. Chemical Abstracts, vol. 135, no. 107343 (2001), Abstract for WO 2001/051469.*
Jones et al. Pharmacology, Biochemistry and Behavior 71, p. 555–568 (2002).*
Robichaud et al. in Annual Reports in medicinal Chemistry, vol. 35, p. 11–20 (2000).*
Hitoshi Oinuma et al:Journal of Medicinal Chemistry, US, American Chemical Society, Washinton, vol. 34, no. 7, Jul. 1, 1991, pp. 2260–2267.

* cited by examiner

*Primary Examiner*—Emily Bernhardt
(74) *Attorney, Agent, or Firm*—L. Eric Thies; Melvin Winokur

(57) ABSTRACT

A class of phenylsulphonyl derivatives wherein the sulphonyl moiety is also attached to an N-arylalkyl-substituted piperazine ring are selective antagonists of the human 5-HT$_{2A}$ receptor and are therefore useful as pharmaceutical agents, especially in the treatment and/or prevention of adverse conditions of the central nervous system, including schizophrenia and other psychotic disorders.

7 Claims, No Drawings

PHENYLSULPHONYLIPIPERAZINYL DERIVATIVES AS 5-HT RECEPTOR LIGANDS

CROSS REFERENCE TO RELATED APPLICATIONS

This application is a U.S. National Phase application under 35 U.S.C. § 371 of PCT Application No. PCT/GB01/01472, which was filed Mar. 30, 2001, and which claims priority under 35 U.S.C. § 119 from GB Application No. 0007907.9, which was filed Mar. 31, 2000.

The present invention relates to a class of sulphonyl derivatives which act on serotonin receptors (also known as 5-hydroxytryptamine or 5-HT receptors). More particularly, the invention concerns phenylsulphonyl derivatives wherein the sulphonyl moiety is also attached to an N-arylalkyl-substituted piperazine ring. These compounds are selective antagonists of the human $5\text{-HT}_{2A}$ receptor and are therefore useful as pharmaceutical agents, especially in the treatment and/or prevention of adverse conditions of the central nervous system, including psychotic disorders such as schizophrenia.

Schizophrenia is a disorder which is conventionally treated with drugs known as neuroleptics. In many cases, the symptoms of schizophrenia can be treated successfully with so-called "classical" neuroleptic agents such as haloperidol. Classical neuroleptics generally are antagonists at dopamine $D_2$ receptors.

Notwithstanding their beneficial antipsychotic effects, classical neuroleptic agents such as haloperidol are frequently responsible for eliciting acute extrapyramidal symptoms (movement disorders) and neuroendocrine (hormonal) disturbances. These side-effects, which plainly detract from the clinical desirability of classical neuroleptics, are believed to be attributable to $D_2$ receptor blockade in the striatal region of the brain.

The compound (+)-α-(2,3-dimethoxyphenyl)-1-[2-(4-fluorophenyl)-ethyl]-4-piperidinemethanol (also known as MDL-100,907) is described in WO 91/18602. In preclinical studies, MDL-100,907 failed to induce catalepsy and failed to block apomorphine-induced stereotyped behaviour in animal models, strongly suggesting that this compound would be free from any liability to cause extrapyramidal side-effects. MDL-100,907 is currently undergoing clinical trials in schizophrenic patients and has demonstrated efficacy in a multicentre, placebo-controlled study for antipsychotic potential, with no neurological adverse effects. Pharmacologically, MDL-100,907 has been shown to be a potent antagonist of human $5\text{-HT}_{2A}$ receptors, whilst being essentially devoid of activity at the human dopamine $D_2$ receptor. It is accordingly believed that compounds which can interact selectively with the $5\text{-HT}_{2A}$ receptor relative to the dopamine $D_2$ receptor will display the beneficial level of antipsychotic activity associated with $5\text{-HT}_{2A}$ receptor antagonism, whilst minimizing or even avoiding the extrapyramidal and other side-effects arising from an interaction with dopamine $D_2$ receptors.

The compounds of the present invention are potent antagonists of the human $5\text{-HT}_{2A}$ receptor, and are accordingly of benefit in the treatment and/or prevention of psychotic disorders such as schizophrenia. The compounds of the invention may display more effective binding to the human $5\text{-HT}_{2A}$ receptor than to the human dopamine $D_2$ receptor, and they can therefore be expected to manifest fewer side-effects than compounds which do not discriminate in their binding affinity as between $5\text{-HT}_{2A}$ and $D_2$ receptors.

By virtue of their potent human $5\text{-HT}_{2A}$ receptor antagonist activity, the compounds of the present invention are also effective in the treatment of neurological conditions including depression, anxiety, panic disorder, obsessive-compulsive disorder, pain, sleep disorders such as insomnia, eating disorders such as anorexia nervosa, and dependency or acute toxicity associated with narcotic agents such as LSD or MDMA; and moreover are beneficial in controlling the extrapyramidal symptoms associated with the administration of neuroleptic agents. They may further be effective in the lowering of intraocular pressure and may therefore be beneficial in treating glaucoma (cf. T. Mano et al. and H. Takaneka et al., *Investigative Ophthalmology and Visual Science,* 1995, vol. 36, pages 719 and 734 respectively).

Being $5\text{-HT}_{2A}$ receptor antagonists, the compounds of the present invention may also be beneficial in preventing or reducing the toxic symptoms associated with the intake of ergovaline in animals consuming *Acremonium coenophialum* infected tall fescue (cf. D. C. Dyer, *Life Sciences,* 1993, 53, 223–228).

The compounds according to the present invention are potent and selective $5\text{-HT}_{2A}$ receptor antagonists having a human $5\text{-HT}_{2A}$ receptor binding affinity ($K_i$) of 100 nM or less, typically of 50 nM or less and preferably of 10 nM or less. The compounds of the invention may possess at least a 10-fold selective affinity, suitably at least a 20-fold selective affinity and preferably at least a 50-fold selective affinity, for the human $5\text{-HT}_{2A}$ receptor relative to the human dopamine $D_2$ receptor.

The present invention provides a compound of formula I, or a salt thereof:

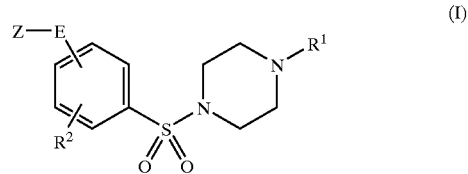

(I)

wherein

Z represents halogen, cyano, nitro, trifluoromethyl, trifluoromethoxy, $-R^a$, $-OR^a$, $-SR^a$, $-SOR^a$, $-SO_2R^a$, $-SO_2NR^aR^b$, $-NR^aR^b$, $-NR^aCOR^b$, $-NR^aCO_2R^b$, $-COR^a$, $-CO_2R^a$ or $-CONR^aR^b$; or Z represents an optionally substituted five-membered heteroaromatic ring selected from furan, thiophene, pyrrole, oxazole, thiazole, isoxazole, isothiazole, imidazole, pyrazole, oxadiazole, thiadiazole, triazole and tetrazole; or Z represents an optionally substituted six-membered heteroaromatic ring selected from pyridine, pyrazine, pyrimidine and pyridazine;

$R^a$ and $R^b$ independently represent hydrogen or $C_{1-6}$ alkyl; or $R^a$ and $R^b$, when linked through a nitrogen atom, together represent the residue of an azetidine, pyrrolidine, piperidine or morpholine ring;

E represents a chemical bond or a straight or branched alkylene chain containing from 1 to 4 carbon atoms, optionally incorporating an oxygen atom to form an ether linkage;

$R^1$ represents an optionally substituted aryl($C_{2-4}$)alkyl group; and $R^2$ represents hydrogen or halogen.

Where Z in the compounds of formula I above represents a five-membered heteroaromatic ring, this ring may be optionally substituted by one or, where possible, two substituents. As will be appreciated, where Z represents an oxadiazole, thiadiazole or tetrazole ring, only one substituent will be possible; otherwise, one or two optional substituents may be accommodated around the five-membered heteroaromatic ring Z.

Where Z in the compounds of formula I above represents a six-membered heteroaromatic ring, this ring may be optionally substituted by one or more substituents, typically by one or two substituents.

Examples of suitable substituents on the five-membered or six-membered heteroaromatic ring as specified for Z include halogen, cyano, trifluoromethyl, $C_{1-6}$ alkyl, $C_{1-6}$ alkoxy, $C_{1-6}$ alkylthio, amino, $C_{1-6}$ alkylamino and di($C_{1-6}$) alkylamino, especially methyl.

The aryl($C_{2-4}$)alkyl group $R^1$ may be optionally substituted by one or more substituents. Suitably, the aryl($C_{2-4}$) alkyl group $R^1$ is unsubstituted, or substituted by one, two or three substituents. More particularly, the aryl($C_{2-4}$)alkyl group $R^1$ may be unsubstituted, or substituted by one or two substituents. Any optional substitution on the aryl($C_{2-4}$)alkyl group $R^1$ will suitably be on the aryl moiety thereof, although substitution on the alkyl moiety thereof is an alternative possibility.

Representative examples of optional substituents on the group $R^1$ include halogen, nitro, trifluoromethyl, trifluoromethoxy, $C_{1-6}$ alkyl, keto, hydroxy, $C_{1-6}$ alkoxy, $C_{1-6}$ alkylthio or di($C_{1-6}$)alkylamino.

As used herein, the expression "$C_{1-6}$ alkyl" includes methyl and ethyl groups, and straight-chained or branched propyl, butyl, pentyl and hexyl groups. Particular alkyl groups are methyl, ethyl, n-propyl, isopropyl and tert-butyl. Derived expressions such as "$C_{1-6}$ alkoxy", "$C_{1-6}$ alkylthio" and "$C_{1-6}$ alkylamino" are to be construed accordingly.

Typical aryl groups include phenyl and naphthyl, preferably phenyl.

The expression "aryl($C_{2-4}$)alkyl" as used herein includes phenylethyl, phenylpropyl and naphthylethyl, especially phenylethyl.

The term "halogen" as used herein includes fluorine, chlorine, bromine and iodine, especially fluorine or chlorine.

For use in medicine, the salts of the compounds of formula I will be pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

Where the compounds according to the invention have at least one asymmetric centre, they may accordingly exist as enantiomers. Where the compounds according to the invention possess two or more asymmetric centres, they may additionally exist as diastereoisomers. It is to be understood that all such isomers and mixtures thereof in any proportion are encompassed within the scope of the present invention.

Typically, the substituent Z in the compounds of formula I above represents hydrogen, halogen, cyano, —$NR^aCOR^b$, —$CO_2R^a$ or —$CONR^aR^b$; or an optionally substituted five-membered ring as specified above.

Suitably, the substituent Z represents hydrogen, halogen, cyano, trifluoromethyl, trifluoromethoxy, —$R^a$ or —$NR^aCOR^b$.

Suitably, $R^a$ represents hydrogen or methyl.

Suitably, $R^b$ represents hydrogen or methyl.

Where the group Z represents an optionally substituted five-membered heteroaromatic ring, this is suitably an imidazole, pyrazole, 1,2,3-triazole, 1,2,4-triazole or tetrazole ring, any of which may be optionally substituted, typically by methyl.

Specific values for the group Z include hydrogen, bromo, cyano, acetylamino, methoxycarbonyl, carboxamido, imidazol-1-yl, pyrazol-1-yl, 1,2,3-triazol-1-yl, 1,2,4-triazol-1-yl, 1-methyl-1,2,4-triazol-5-yl, tetrazol-1-yl and 2-methyltetrazol-5-yl.

Particular values for the group Z include hydrogen, fluoro, chloro, cyano, trifluoromethyl, trifluoromethoxy, methyl or acetylamino.

One specific value of Z is carboxamido.

Another specific value of Z is cyano.

Where E represents a straight or branched alkylene chain, this may be, for example, methylene, ethylene, 1-methylethylene, propylene, 2-methylpropylene or butylene. The alkylene chain E may optionally incoporate an oxygen atom, thereby forming an ether linkage. Moreover, E may represent a chemical bond such that the moiety Z is attached directly to the phenyl ring as depicted in formula I above.

Preferably, E represents a chemical bond or a methylene linkage.

In a specific embodiment, E represents a chemical bond.

Suitably, $R^1$ represents optionally substituted phenylethyl or optionally substituted phenylpropyl. In addition, $R^1$ may represent optionally substituted naphthylethyl.

Preferably, $R^1$ represents phenylethyl, which may be unsubstituted, or substituted by one or more substituents. Typically, the phenylethyl group $R^1$ will be unsubstituted, or substituted by one, two or three (especially one or two) substituents. In a particular embodiment, $R^1$ represents disubstituted phenylethyl.

Examples of specific substituents on the group $R^1$ include fluoro, chloro, bromo, iodo, nitro, trifluoromethyl, methyl, keto, hydroxy, methoxy, methylthio and dimethylamino.

Specific examples of optional substituents on $R^1$ include fluoro, chloro and keto, especially fluoro.

Representative values of $R^1$ include phenylethyl, fluoro-phenylethyl, chloro-phenylethyl, bromo-phenylethyl, iodo-phenylethyl, difluoro-phenylethyl, dichloro-phenylethyl, (chloro)(fluoro)-phenylethyl, (fluoro)-(trifluoromethyl)-phenylethyl, (bromo)(methoxy)-phenylethyl, trifluoro-phenylethyl, nitro-phenylethyl, methyl-phenylethyl, hydroxy-phenylethyl, methoxy-phenylethyl, dimethoxy-phenylethyl, (hydroxy)(methoxy)-phenylethyl, (hydroxy) (dimethoxy)-phenylethyl, trimethoxy-phenylethyl, methylthio-phenylethyl, dimethylamino-phenylethyl, phenylpropyl, hydroxy-phenylpropyl, naphthylethyl, fluorophenyl-oxoethyl and chlorophenyl-oxoethyl.

Typical values of $R^1$ include phenylethyl, fluoro-phenylethyl, chloro-phenylethyl, difluoro-phenylethyl, fluorophenyl-oxoethyl and chlorophenyl-oxoethyl.

Particular values of $R^1$ include phenylethyl, fluoro-phenylethyl, chloro-phenylethyl and difluoro-phenylethyl.

Suitably, $R^1$ may represent 2-phenylethyl, 2-fluoro-2-phenylethyl, 2-(4-fluorophenyl)ethyl, 2-(2-chlorophenyl) ethyl, 2-(2,4-difluorophenyl)ethyl, 2-(4-fluorophenyl)-2-oxoethyl or 2-(4-chlorophenyl)-2-oxoethyl.

One specific value of $R^1$ is 2-(2,4-difluorophenyl)ethyl.

Another specific value of $R^1$ is 2-(4-fluorophenyl)-2-oxoethyl.

Suitably, $R^2$ represents hydrogen or fluoro, especially hydrogen.

A particular sub-class of compounds according to the invention is represented by the compounds of formula IA, and salts thereof:

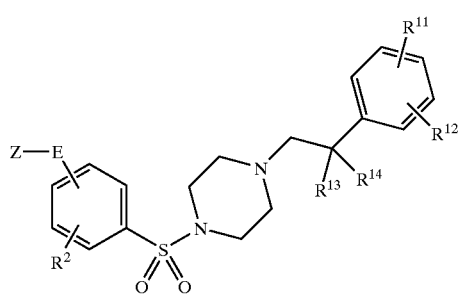
(IA)

wherein

Z and E are as defined with reference to formula I above;

$R^{11}$ and $R^{12}$ independently represent hydrogen, halogen, nitro, trifluoromethyl, $C_{1-6}$ alkyl, hydroxy, $C_{1-6}$ alkoxy, $C_{1-6}$ alkylthio or di($C_{1-6}$)alkylamino;

$R^{13}$ represents hydrogen and $R^{14}$ represents hydrogen or fluoro, or $R^{13}$ and $R^{14}$ together represent keto; and $R^{21}$ represents hydrogen, fluoro or chloro, suitably hydrogen or fluoro.

Suitably, $R^{11}$ represents hydrogen, fluoro, chloro or methoxy, especially hydrogen or fluoro.

Suitably, $R^{12}$ represents hydrogen, fluoro, chloro, bromo, iodo, nitro, trifluoromethyl, methyl, hydroxy, methoxy, methylthio or dimethylamino. More particularly, $R^{12}$ may represent hydrogen, fluoro or chloro.

In one embodiment of the compounds of formula IA above, $R^{13}$ represents hydrogen and $R^{14}$ represents hydrogen or fluoro.

In another embodiment of the compounds of formula IA, $R^{13}$ and $R^{14}$ together represent keto.

Suitably, $R^{13}$ and $R^{14}$ are both hydrogen.

Suitably, $R^{21}$ is hydrogen or chloro, especially hydrogen.

Another sub-class of compounds according to the invention is represented by the compounds of formula IB, and salts thereof:

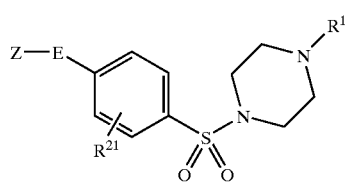
(IB)

wherein Z, E and $R^1$ are as defined with reference to formula I above; and $R^{21}$ is as defined with reference to formula IA above.

A particular subset of the compounds of formula IA and IB above is represented by the compounds of formula IC, and salts thereof:

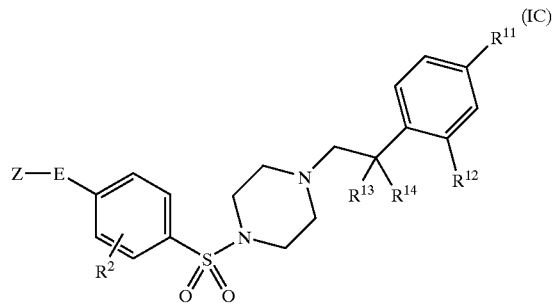
(IC)

wherein Z, E, $R^{11}$, $R^{12}$, $R^{13}$, $R^{14}$ and $R^{21}$ are as defined above.

In one embodiment of the compounds of formula IC above, $R^{13}$ and $R^{14}$ are both hydrogen.

Specific compounds within the scope of the present invention include the compounds whose preparation is described in the accompanying Examples, and salts thereof.

The invention also provides pharmaceutical compositions comprising one or more of the compounds according to this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. Alternatively, the compositions may be presented in a form suitable for once-weekly or once-monthly administration; for example, an insoluble salt of the active compound, such as the decanoate salt, may be adapted to provide a depot preparation for intramuscular injection. An erodible polymer containing the active ingredient may be envisaged. For preparing solid compositions such as tablets, the principal active ingredient is mixed with a pharmaceutical carrier, e.g. conventional tableting ingredients such as corn starch,actose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. Favoured unit dosage forms contain from 1 to 100 mg, for example 1, 2, 5, 10, 25, 50 or 100 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

In the treatment of schizophrenia, a suitable dosage level is about 0.01 to 250 mg/kg per day, preferably about 0.05 to 100 mg/kg per day, and especially about 0.05 to 5 mg/kg per day. The compounds may be administered on a regimen of 1 to 4 times per day.

If desired, the compounds according to this invention may be co-administered with another anti-schizophrenic medicament, for example one producing its effects via dopamine $D_2$ and/or $D_4$ receptor subtype blockade. In such circumstances, an enhanced anti-schizophrenic effect may be envisaged without a corresponding increase in side-effects such as those caused by, for example, $D_2$ receptor subtype blockade; or a comparable anti-schizophrenic effect with reduced side-effects may alternatively be envisaged. Such co-administration may be desirable where a patient is already established on an anti-schizophrenic treatment regime involving conventional anti-schizophrenic medicaments. Suitable anti-schizophrenic medicaments of use in combination with the compounds according to the present invention include haloperidol, chlorpromazine, mesoridazine, thioridazine, acetophenazine, fluphenazine, perphenazine, trifluoperazine, chloroprothixene, thiothixene, clozapine, olanzapine, pimozide, molindone, oxapine, sulpiride, risperidone, xanomeline, fananserin and ziprasidone, and pharmaceutically acceptable salts thereof.

The compounds according to the present invention may be prepared by a process which comprises the reaction of a compound of formula II with a compound of formula III:

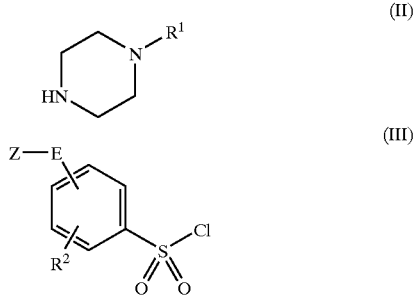

wherein $R^1$, $R^2$, Z and E are as defined above.

The reaction is conveniently effected by heating the reagents at reflux in the presence of a base such as potassium carbonate, and a suitable solvent such as acetonitrile.

The compounds of formula II may be prepared by reducing a compound of formula IV:

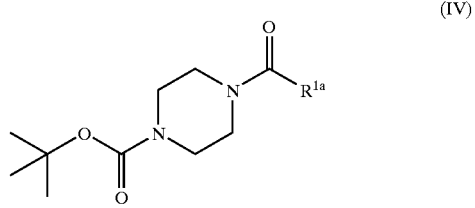

wherein —$CH_2R^{1a}$ corresponds to the moiety $R^1$ as defined above; followed by removal of the tert-butoxycarbonyl (BOC) protecting group.

The reduction of compound IV is conveniently effected by treatment with a reducing agent such as $BH_3.THF$, typically by heating at reflux in a suitable solvent, e.g. tetrahydrofuran.

Subsequent removal of the BOC protecting group is conveniently effected by treatment with a mineral acid, e.g. 6N HCl.

The compounds of formula IV may be prepared by reacting the compound of formula V with a compound of formula VI:

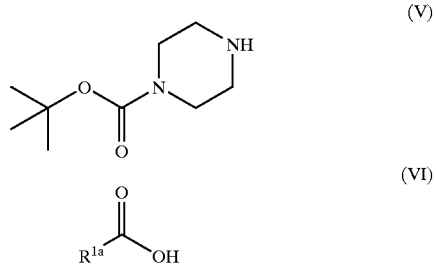

wherein $R^{1a}$ is as defined above; in the presence of a condensing agent.

The reaction is conveniently effected at room temperature in the presence of a suitable solvent such as dichloromethane. The condensing agent is preferably water soluble carbodiimide, in which case the reaction is conveniently effected in the presence of 1-hydroxybenzotriazole and optionally an organic base such as triethylamine.

The compounds according to the present invention may also be prepared by rapid analogue synthesis. This preparation involves the reaction of a compound of formula II as defined above with a small excess, typically 1.2 equivalents, of a compound of formula III as defined above, at room temperature, in the presence of a base, e.g. 2N NaOH, and a suitable solvent such as dichloromethane; followed by removal of the excess amount of the compound of formula III by utilising a suitable sulphonyl chloride scavenger resin, e.g. aminomethylated polystyrene EHL (200–400 mesh).

The compound of formula VI is commercially available from the Sigma-Aldrich Company Ltd., Dorset, United Kingdom.

Where they are not commercially available, the starting materials of formula III and VI may be prepared by procedures analogous to those described in the accompanying Examples, or by standard methods well known from the art.

It will be appreciated that any compound of formula I initially obtained from any of the above processes may, where appropriate, subsequently be elaborated into a further desired compound of formula I using techniques known from the art. For example, a compound of formula I initially obtained wherein the moiety Z-E- represents bromo may be converted into the corresponding compound of formula I wherein the moiety Z-E- represents cyano by treatment with copper(I) cyanide in the presence of 1-methyl-2-pyrrolidinone (NMP), or with zinc cyanide in the presence of tetrakis(triphenylphosphine)palladium(0). The resulting compound of formula I wherein the moiety Z-E- represents cyano thereby obtained may in turn be converted into the corresponding compound of formula I wherein the moiety Z-E- represents carboxamido by heating in mineral acid, e.g. 85% sulphuric acid at 100° C., or by treatment with potassium trimethylsilanolate, typically in tetrahydrofuran at reflux. Alternatively, a compound of formula I initially obtained wherein the moiety Z-E- represents bromo may be converted directly into the corresponding compound of formula I wherein the moiety Z-E- represents carboxamido by heating under a carbon monoxide atmosphere in the presence of 1,1,1,3,3,3-hexamethyldisilazane, diisopropylamine, palladium(II) acetate and 1,3-bis(diphenylphosphino)propane. Where, for example, the moiety Z-E- in the compounds of formula I represents an optionally substituted N-linked pyrrole, imidazole, pyrazole, triazole or tetrazole moiety, e.g. imidazol-1-yl, pyrazol-1-yl, 1,2,3-triazol-1-yl or 1,2,4-triazol-1-yl, these compounds may be prepared by treating the corresponding compound of formula I wherein Z-E- represents bromo with the appropriate optionally substituted pyrrole, imidazole, pyrazole, triazole or tetrazole derivative, in the presence of copper bronze and sodium hydride, typically with heating in NMP. Where, for example, the moiety Z-E- in the compounds of formula I represents an optionally substituted C-linked five-membered heteroaromatic ring, e.g. 2-methyltetrazol-5-yl or 1-methyl-1,2,4-triazol-5-yl, these compounds may be prepared by reacting the corresponding compound of formula I wherein Z-E- represents bromo with a tributylstannyl derivative of the appropriate heteroaromatic compound, e.g. 2-methyl-5-tributylstannyltetrazole or 1-methyl-5-tributylstannyl-1,2,4-triazole, in the presence of a transition metal catalyst such as tetrakis(triphenylphosphine)palladium(0), typically with heating in a solvent such as N,N-dimethylformamide. A compound of formula I wherein, for example, Z represents a tetrazol-1-yl moiety and E is methylene may be prepared from the corresponding compound of formula I wherein the moiety Z-E- represents hydroxymethyl, by mesylation under standard conditions followed by displacement of the mesyl group by treatment with tetrazole, typically in the presence of sodium iodide and a base such as caesium carbonate; the compound of formula I wherein Z-E- represents hydroxymethyl may suitably be prepared by diisobutylaluminium hydride (DIBAL-H) reduction of the corresponding compound of formula I wherein Z-E- represents a $C_{2-6}$ alkoxycarbonyl group, e.g. methoxycarbonyl, which in turn may be prepared by treatment of the corresponding compound of formula I wherein Z-E- represents bromo with 1,1'-bis(diphenylphosphino)ferrocene, palladium(II) acetate, triethylamine and a $C_{1-6}$ alkanol such as methanol, in an atmosphere of carbon monoxide. A compound of formula I wherein Z-E- represents $C_{2-6}$ alkoxycarbonyl, e.g. methoxycarbonyl, may be converted to the corresponding compound of formula I wherein Z-E- represents carboxamido by treatment with ammonium chloride in the presence of trimethylaluminium.

Where the above-described processes for the preparation of the compounds of use in the invention give rise to mixtures of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques such as preparative HPLC, or the formation of diastereomeric pairs by salt formation with an optically active acid, such as (−)-di-p-toluoyl-d-tartaric acid and/or (+)-di-p-toluoyl-l-tartaric acid, followed by fractional crystallization and regeneration of the free base. The compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

The following Examples illustrate the preparation of compounds of use in the invention.

The compounds in accordance with this invention potently inhibit [$^3$H]-ketanserin binding to the human 5-HT$_{2A}$ receptor expressed in clonal cell lines. Moreover, those compounds of the invention which have been tested display a selective affinity for the 5-HT$_{2A}$ receptor relative to the dopamine D$_2$ receptor.

The compounds of the accompanying Examples were all found to possess a K$_i$ value for displacement of [$^3$H]-ketanserin from the human 5-HT$_{2A}$ receptor, when expressed in Chinese hamster ovary (CHO) clonal cell lines, of 100 nM or less.

EXAMPLE 1

1-[2-(2,4-Difluorophenyl)ethyl]-4-phenylsulphonylpiperazine 2,4-Difluorophenylacetic acid (10 g, 59.04 mmol), 1-hydroxybenzotriazole (9.04 g, 59.04 mmol), water soluble carbodiimide (10.16 g, 59.04 mmol) and NEt$_3$ (5.97 ml, 59.04 mmol) were stirred in dichloromethane (60 ml) for 15 min. BOC-piperazine (5.41 g, 29.52 mmol) was added and the mixture stirred at room temperature for 8 h. Reaction progress was monitored by TLC. The reaction mixture was diluted with dichloromethane (20 ml) and washed with aqueous 1N NaOH, followed by 1M citric acid. The organic phase was separated, dried (MgSO$_4$) and concentrated to yield a white crystalline solid (78%). $\delta_H$ (250 MHz, CDCl$_3$): 1.47 (9H, s), 3.36–3.42 (4H, m), 3.42–3.52 (2H, m), 3.58–3.66 (2H, m), 3.75 (2H, s), 6.78–6.90 (2H, m), 7.21–7.31 (1H, m).

The foregoing product (7.8 g, 22.9 mmol) was dissolved in THF (60 ml) and BH$_3$.THF (36.64 ml, 36.64 mmol, 1M solution in THF) was added. The reaction was refluxed, and monitored by TLC and mass spectroscopy. The reaction was treated with 6N HCl (250 ml) and refluxed for a further 2 h. The aqueous reaction mixture was washed with ether, then concentrated. The acidic solution was basified and extracted into dichloromethane (3×70 ml). The organic extracts were combined, dried (MgSO$_4$), and concentrated to give 1-[2-(2,4-difluorophenyl)ethyl]piperazine. Purified by flash chromatography. Yield 50%. MS: (M+H)$^+$=227. $\delta_H$ (360 MHz, CDCl$_3$): 2.44–2.60 (5H, m), 2.75–2.85 (2H, m), 2.92–3.14 (6H, bs, m), 6.72–6.82 (2H, m), 7.12–7.20 (1H, m).

Benzene sulphonyl chloride (0.15 g), the foregoing amine (0.193 g) and potassium carbonate (0.118 g) were heated together in MeCN (10 ml). Reaction was monitored by mass spectroscopy, and was completed after 2 h. The reaction mixture was cooled to room temperature, quenched with water and extracted into ethyl acetate. The organic extracts were combined, washed with water, dried (MgSO$_4$) and concentrated to give a dark orange solid. This solid was purified by dry flash chromatography using SiO$_2$, CH$_2$Cl$_2$ to 5% MeOH:CH$_2$Cl$_2$, followed by recrystallisation using pet. ether and CH$_2$Cl$_2$ to give the title product as a pale yellow solid (23%). MS: (M+H)$^+$=367. $\delta_H$ (360 MHz, CDCl$_3$): 2.50–2.60 (6H, m), 2.66–2.74 (2H, m), 3.02–3.10 (4H, m), 6.70–6.80 (2H, m), 7.05–7.14 (1H, m), 7.50–7.56 (2H, m), 7.56–7.62 (1H, m), 7.74–7.80 (2H, m). CHN C$_{18}$H$_{20}$F$_2$N$_2$O$_2$S: calc. C=59.00, H=5.50, N=7.65%; found C=59.12, H=5.43, N=7.56%.

GENERALISED EXAMPLE

Rapid Analogue Synthesis

1-[2-(2,4-Difluorophenyl)ethyl]piperazine (3.2 g) was dissolved in dichloromethane (64 cm) and divided equally into 64 reaction tubes. To each reaction tube was added 2N NaOH (1.5 eq), followed by a solution of the sulphonyl chloride (1.2 eq) in dichloromethane (1 cm). The tubes were sealed with screw-on caps, and mixed together in a reaction shaker at room temperature for a 48 h period. Reactions were monitored by mass spectrometry. The aqueous and organic layers were separated using PTFE filter cartidges which retain the aqueous layers.

The organic phases were collected in tubes which contain the sulphonyl chloride scavenger resin, aminomethylated polystyrene EHL (200–400 mesh) (50 mg in each tube). The mixtures were shaken at room temperature for 2 h. After this period, the resins were filtered off and the organic phases were collected in pre-weighed tubes. Solvent was evaporated under a down flow of nitrogen gas at 40° C. Resultant products were analysed by $^1$H NMR (400 MHz, CDCl$_3$).

EXAMPLES 2 TO 14

The following Examples were produced by methods analogous to those described above:

| Example No. | Structure |
|---|---|
| 2 | 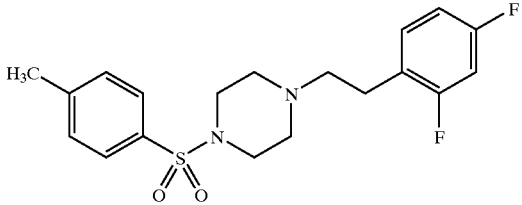 |
| 3 | 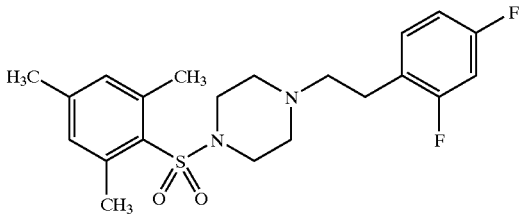 |
| 4 | 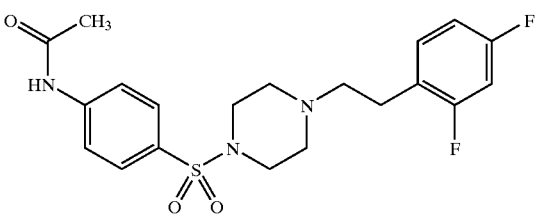 |
| 5 | 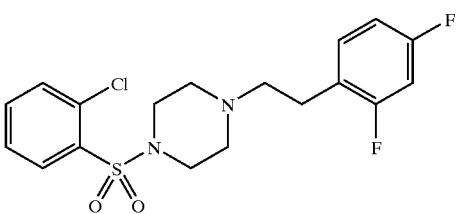 |

-continued

| Example No. | Structure |
|---|---|
| 6 | 2-(trifluoromethyl)phenylsulfonyl-piperazine-N-CH₂CH₂-(2,4-difluorophenyl) |
| 7 | 2,6-dichlorophenylsulfonyl-piperazine-N-CH₂CH₂-(2,4-difluorophenyl) |
| 8 | 2-(trifluoromethoxy)phenylsulfonyl-piperazine-N-CH₂CH₂-(2,4-difluorophenyl) |
| 9 | 3-fluorophenylsulfonyl-piperazine-N-CH₂CH₂-(2,4-difluorophenyl) |
| 10 | 2-methyl-6-chlorophenylsulfonyl-piperazine-N-CH₂CH₂-(2,4-difluorophenyl) |
| 11 | 3-chloro-2-methylphenylsulfonyl-piperazine-N-CH₂CH₂-(2,4-difluorophenyl) |
| 12 | 2-cyanophenylsulfonyl-piperazine-N-CH₂CH₂-(2,4-difluorophenyl) |

| Example No. | Structure |
|---|---|
| 13 | 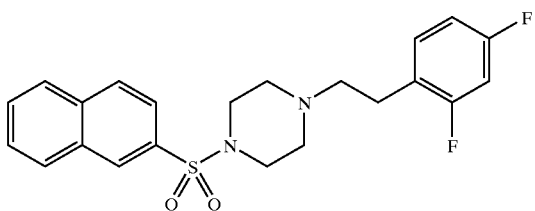 |
| 14 | 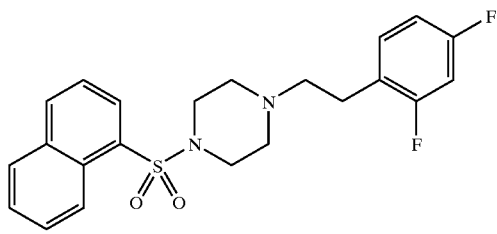 |

What is claimed is:

1. A compound of formula I, or a pharmaceutically acceptable salt thereof:

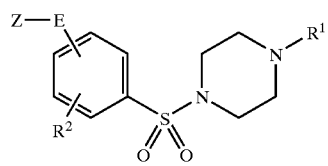

(I)

wherein:

Z is selected from the group consisting of halogen, hydrogen cyano, nitro, trifluoromethyl, trifluoromethoxy, $-OR^a$, $-SR^a$, $-SOR^a$, $-SO_2R^a$, $-SO_2NR^aR^b$, $-NR^aR^b$, $-NR^aCOR^b$, $-NR^aCO_2R^b$, $-COR^a$, $-CO_2R^a$ and $-CONR^aR^b$; or $R^a$ and $R^b$ are independently selected from hydrogen and $C_{1-6}$ alkyl; or $R^a$ and $R^b$, when linked through a nitrogen atom, together represent the residue of an azetidine, pyrrolidine, piperidine or morpholine ring;

E represents a chemical bond or a straight or branched alkylene chain having from 1 to 4 carbon atoms, optionally incorporating an oxygen atom to form an ether linkage;

$R^1$ represents an aryl($C_{2-4}$)alkyl group, which is unsubstituted or substituted with a substituent selected from: halogen, nitro, trifluoromethyl, trifluoromethoxy, $C_{1-6}$ alkyl, keto, hydroxy, $C_{1-6}$ alkoxy, $C_{1-6}$ alkylthio, and di($C_{1-6}$)alkylamino; and $R^2$ represents hydrogen or halogen; with the proviso that the compound is other than 1-[[4-(methylamino)phenyl]-sulfonyl]-4-[2-phenylethyl]piperazine.

2. The compound of claim 1 of the formula IA, or a pharmaceutically acceptable salt thereof:

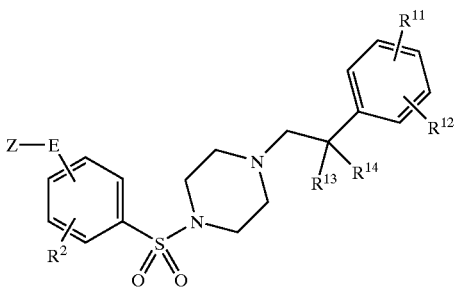

(IA)

wherein $R^{11}$ and $R^{12}$ are each independently selected from the group consisting of hydrogen, halogen, nitro, trifluoromethyl, $C_{1-6}$ alkyl, hydroxy, $C_{1-6}$ alkoxy, $C_{1-6}$ alkylthio and di($C_{1-6}$)alkylamino;

$R^{13}$ represents hydrogen and $R^{14}$ represents hydrogen or fluoro, or $R^{13}$ and $R^{14}$ together represent keto; and $R^{21}$ is selected from the group consisting of hydrogen, fluoro and chloro.

3. The compound of claim 1 of the formula IB, or a pharmaceutically acceptable salt thereof:

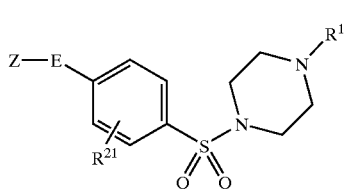

(IB)

wherein $R^{21}$ is selected from the group consisting of hydrogen, fluoro and chloro.

4. The compound of claim 2 of the formula IC:
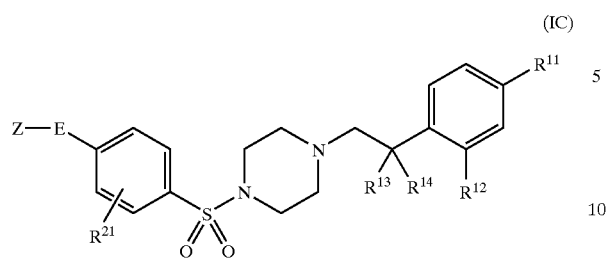
or a pharmaceutically acceptable salt thereof.
5. A compound which is selected from the group consisting of: 1-[2-(2,4-difluorophenyl)ethyl]-4-phenylsulphonylpiperazine;
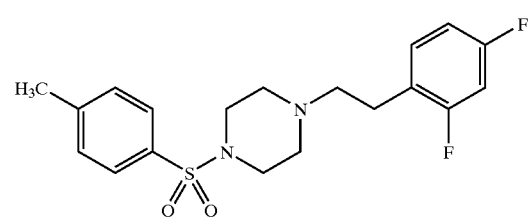
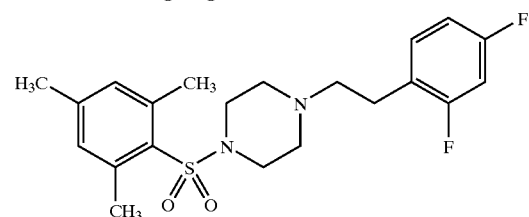
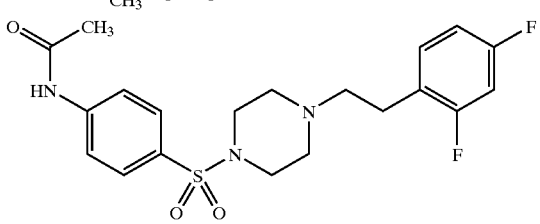
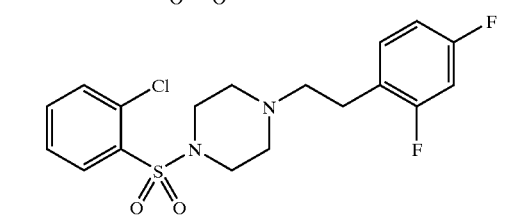
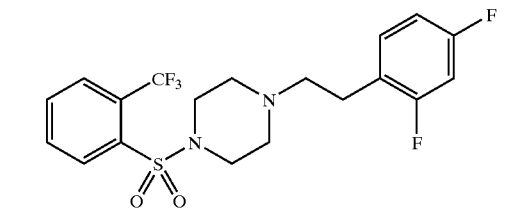
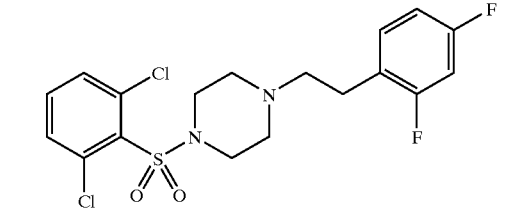
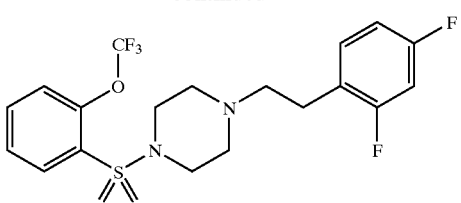
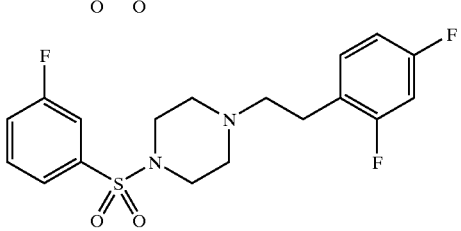
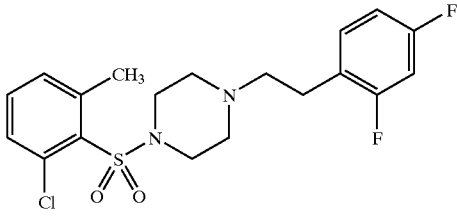
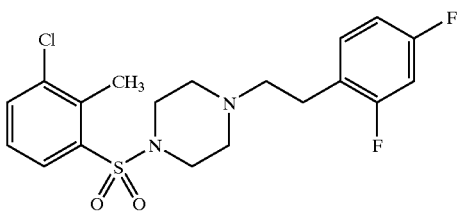
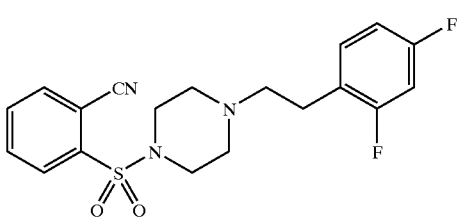
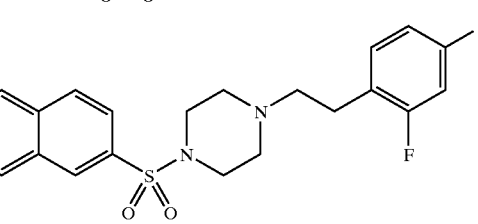
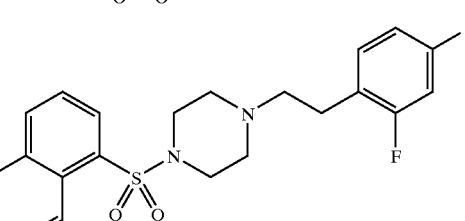
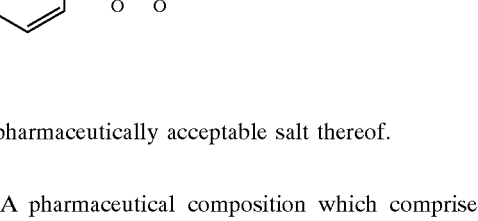
or a pharmaceutically acceptable salt thereof.
6. A pharmaceutical composition which comprises an inert carrier and the compound of claim 1.

7. A method for the treatment of a disorder which is selected from the group consisting of: schizophrenia, depression, anxiety, panic disorder, obsessive-compulsive disorder, and insomnia, in a mammalian patient in need of such treatment which comprises administering to the patient a therapeutically effective amount of a compound of claim 1.

* * * * *